United States Patent [19]

Rosa et al.

[11] Patent Number: 4,668,821

[45] Date of Patent: May 26, 1987

[54] METHOD FOR EXTRACTING PHENYLALANINE FROM BROTHS OF BIOCONVERSION

[75] Inventors: Onorino G. Rosa, To; Carlo Varesio, Turin; Ernesto Oppici, Milan, all of Italy

[73] Assignee: Farmitalia Carlo Erba S.p.A., Milan, Italy

[21] Appl. No.: 827,676

[22] Filed: Feb. 10, 1986

Related U.S. Application Data

[63] Continuation of Ser. No. 638,514, Aug. 7, 1984, abandoned.

[30] Foreign Application Priority Data

May 31, 1984 [IT] Italy ................................ 21196 A/84

[51] Int. Cl.⁴ .............................................. C07C 99/12
[52] U.S. Cl. ................................................... 562/443
[58] Field of Search ................. 562/441, 445; 435/108

[56] References Cited

U.S. PATENT DOCUMENTS

| | | | |
|---|---|---|---|
| 2,894,954 | 7/1959 | De Witt et al. | 562/445 |
| 3,917,511 | 11/1975 | Nakayama et al. | 435/108 |
| 4,384,136 | 5/1983 | Steinmetzer | 562/445 |
| 4,407,952 | 10/1983 | Tsuchida et al. | 435/108 |

FOREIGN PATENT DOCUMENTS

| | | | |
|---|---|---|---|
| 56-26197 | 9/1979 | Japan | 435/108 |
| 59-74994 | 4/1984 | Japan | 435/108 |
| 1489468 | 10/1977 | United Kingdom | 562/343 |

*Primary Examiner*—James H. Reamer
*Attorney, Agent, or Firm*—Oblon, Fisher, Spivak, McClelland & Maier

[57] ABSTRACT

The invention discloses a method for extracting phenylalanine from the broths obtained by enzymatic processes; this method consists in flocculating and filtering the broth, concentrating the filtrate followed by filtering off the resulting cinnamic acid, decolorating and concentrating the filtrate to obtain phenylalanine crystals at a very pure degree.

6 Claims, No Drawings

METHOD FOR EXTRACTING PHENYLALANINE FROM BROTHS OF BIOCONVERSION

This application is a continuation of application Ser. No. 638,514, filed Aug. 7, 1984, now abandoned.

The present invention relates to a method for extracting phenylalanine from the broths obtained by enzymatic processes for preparing phenylalanine.

According to the method of the invention, a very pure compound is obtained with high yields.

The preparation of phenylalanine by enzymatic conversion of cinnamic acid with phenylalanine-ammonialiasis (PAL) is disclosed in the literature.

At the end of the enzymatic process, phenylalanine so obtained is extracted from the broths containing it and purified so as to obtain a compound having a purity corresponding to that required.

Since one of the most important uses of phenylalanine is as an intermediate in the aspartame synthesis, a known alimentary sweetening agent, a very high purity is required to avoid undesired substances being present.

The extraction of phenylalanine from the broths has been up to now effected according to complicated processes with many disadvantages; the process of the invention is a remarkable improvement in comparison with the known processes.

According to the process of the invention, it is possible to obtain, in fact, a very pure product, also as far as the color and limpidity of the aqueous solutions is concerned, which is far better than that before obtained. Furthermore, the process of the invention has the big advantage of not using solvent and, therefore, the obtained phenylalanine does not contin any trace of solvents being particularly suitable for the preparation of aspartame, otherwise contaminated by undesired substances.

A further advantage of the process of the invention consists in obtaining a compound having constant quality, independent of the type of the starting broth.

The extraction process according to the invention essentially consists in the following steps:
flocculation and filtration
concentration to eliminate ammonia
acidification and separation of cinnamic acid
decoloration and concentration to obtain phenylalanine.

The first step of the process of the invention consists in carrying out the flocculation of the broth, obtained by enzymatic conversion, to eliminate most of the impurities contained therein. For this purpose, the broth containing phenylalanine, ammonium carbonate and residual cinnamic acid is added to a flocculating agent, such as calcium hydroxide optionally in the presence of ammonium phosphate, magnesium hydroxide, a siliceous additive (i.e. Sipernat ®) or a decoloring earth (i.e. Tonsil ®) and, preferably, a filtration adjuvant, such as Dicalite ®.

After stirring for a short time, the mixture is filtered and the filtrate heated to a temperature of 40°-70° C. is concentrated in vacuo. It has been found that the preferable concentration to be reached is from 40 g/l to 80 g/l in phenylalanine. In the following step, the obtained solution is acidified to pH of from 2 to 3 to isolate cinnamic acid. Preferably, a strong inorganic acid is used, such as 35%-45% sulphuric acid at a temperature of from 3° to 15° C., under stirring for some hours. Cinnamic acid so obtained is separated by filtration.

The filtrate is decolored in known manner with a decoloring agent, such as decoloring carbon (Ceca 50 SL, Carbon Anticromos ®), in a quantity of from 2% to 15%, which is then eliminated by filtration. The pH value is adjusted to 2.5–4 with sodium, potassium or ammonium hydroxide.

The filtrate is concentrated in vacuo, at a temperature of 40°-80° C. to obtain a concentration of 150–220 g/l of phenylalanine. The pH value is adjusted to 5–6.5 by addition of sodium, potassium or ammonium hydroxide, the solution is cooled to a temperature of from 3° to 15° C., under stirring and phenylalanina precipitates in crystalline forms and is separated in known manner.

A compound is obtained with very high purity and in high yields.

The examples illustrate the invention.

EXAMPLE 1

1 l of broth containing 38 g of phenylalanine 8 g of cinnamic acid was added with 4% of calcium hydroxide in the form of fine powder and 1% of Dicalite ®.

The mixture was kept under stirring for 1 hour, then filtered and the panel was washed with 100 ml of $H_2O$.

The filtrate was concentrated in vacuo to 70 g/l at a temperature of 60° C. The pH value was adjusted to 2.5 by addition of 40% sulphuric acid and the mixture was kept under stirring for 2 hours at 10° C.

Cinnamic acid so obtained was eliminated by filtration, the precipitate was washed with 50 ml of $H_2O$ acidified to pH 2.5 with sulfuric acid.

7.1 g of cinnamic acid was obtained.

The filtered solution was added with decoloring carbon, in a quantity of 5% in respect to phenylalanine; the mixture was kept under stirring for 1 hour and the carbon was eliminated by filtration. pH was adjusted to 2.8 with 30% NaOH and the solution was concentrated in vacuo, at 50° C., to 200 g/l. pH was brought to 6 by addition of 30% NaOH and the reaction mixture was cooled to 5° C., by keeping under stirring for 2 hours.

Phenylalanine crystals were separated by filtration and washed with 110 ml of water. A second drop was obtained from the mother liquors. The precipitates were combined and dried at 45° C., for 6 hours in vacuo.

Phenylalanine was obtained in the yield of 88%.

$[\alpha]^{20}$: $-33,2$ (C=2 water)

Transmittance 660 nm $\geq 95\%$.

Protonometric titer $\geq 99\%$

EXAMPLE 2

1 l of broth containing 34 g of phenylalanine and 9.5 g of cinnamic acid was added with 2% of the decoloring earth, Tonsil ®, and keeping under stirring for 4 hours.

The solution obtained by filtration, was concentrated to 80 g/l, in vacuo, at the temperature of 50° C.

After adjusting the pH of 2.6 with 40% sulfuric acid the mixture was kept under stirring for 4 hours, at 2° C. Cinnamic acid, so obtained (8.6 g), was eliminated by filtration.

Decoloring carbon was added to the filtrate in the quantity of 10% in respect to phenylalanina and after 1 hour stirring the carbon was eliminated by filtration, pH was adjusted to 3.2 with 30% NaOH. The solution was concentrated in vacuo, at 70° C., to 190 g/l.

The pH value was brought to 5,5 and the reaction mixture was cooled to 3° C. Phenylalanine was separated, washed and dried as 45° C. in vacuo.

EXAMPLE 3

Operating as in Example 1, cinnamic acid was eliminated and the filtrate was decolorated with carbon, concentrated to 220 g/l, pH was adjusted to 6.5 with sodium hydroxide, the reaction mixture was cooled to 3° C. to obtain a precipitate of phenylalanine which is separated by filtration.

What we claim is:

1. A process for extracting phenylalanine from a broth containing the same, obtained by the enzymatic conversion of cinnamic acid, comprising:
   (a) flocculating and filtering the broth;
   (b) concentrating the filtrate to 40–80 g/l of phenylalanine;
   (c) acidifying the filtrate to a pH of 2–3, and separating by filtration the cinnamic acid so obtained;
   (d) decoloring the filtrate by a decoloring agent; and
   (e) concentrating the filtrate so obtained to a concentration of 150–220 g/l in phenylalanine, adjusting the pH to 5–6.5 and separating the phenylalanine which precipitates in crystalline form.

2. The process according to claim 1, wherein the flocculation is carried out by the addition of calcium hydroxide, optionally in the presence of ammonium phosphate, magnesium hydroxide, a siliceous additive or decoloring earth and the mixture is kept under stirring for a short time.

3. The process according to claim 1, wherein the broth after flocculation is filtered and the filtrate is heated to 40°–70° C. and is concentrated in vacuo up to a concentration of 40–80 g/l in phenylalanine.

4. The process according to claim 1, wherein the acidification of the concentrated filtrate is effected by the addition of a strong inorganic acid to obtain a pH of 2–3, while stirring, at a temperature of from 3° to 15° C., and isolating the obtained cinnamic acid by filtration.

5. The process according to claim 1, wherein the obtained filtrate, decolored by a decoloring agent, is concentrated in vacuo at a temperature of 40°–80° C. up to a concentration of 150 g–220 g/l in phenylalanine, the pH is subsequently adjusted to 5–6.5, the solution is then cooled to 3°–15° C., under stirring, to obtain phenylalanine in the form of crystals.

6. A process for extracting phenylalanine from a broth containing the same, obtained by the enzymatic conversion of cinnamic acid, consisting essentially of:
   (a) flocculating and filtering the broth;
   (b) concentrating the filtrate to 40–80 g/l of phenylalanine;
   (c) acidifying the filtrate to a pH of 2–3, and separating by filtration the cinnamic acid so obtained;
   (d) decoloring the filtrate by a decoloring agent; and
   (e) concentrating the filtrate so obtained to a concentration of 150–220 g/l in phenylalanine, adjusting the pH to 5–6.5 and separating the phenylalanine which precipitates in crystalline form.

* * * * *